US011116583B2

(12) United States Patent
Loke et al.

(10) Patent No.: US 11,116,583 B2
(45) Date of Patent: Sep. 14, 2021

(54) SURGICAL TRACKING DEVICE AND INSTRUMENT (71) Applicants: Robert M. Loke, Memphis, TN (US); Jerald L. Redmond, Germantown, TN (US); Nikita Pandey, Denver, CO (US); Matthew T. Marrapode, Memphis, TN (US)

(72) Inventors: Robert M. Loke, Memphis, TN (US); Jerald L. Redmond, Germantown, TN (US); Nikita Pandey, Denver, CO (US); Matthew T. Marrapode, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 272 days.

(21) Appl. No.: 15/798,018

(22) Filed: Oct. 30, 2017

(65) Prior Publication Data
US 2019/0125452 A1 May 2, 2019

(51) Int. Cl.
*A61B 34/20* (2016.01)
*A61B 17/17* (2006.01)
*A61B 90/00* (2016.01)
*A61F 2/46* (2006.01)

(52) U.S. Cl.
CPC .......... *A61B 34/20* (2016.02); *A61B 17/1703* (2013.01); *A61B 90/39* (2016.02); *A61B 2034/2055* (2016.02); *A61B 2034/2072* (2016.02); *A61B 2090/376* (2016.02); *A61B 2090/3966* (2016.02); *A61B 2090/3983* (2016.02); *A61F 2/4611* (2013.01)

(58) Field of Classification Search
CPC ............ A61B 34/20; A61B 2090/3983; A61B 2034/2055
See application file for complete search history.

(56) References Cited

U.S. PATENT DOCUMENTS

| | | | | |
|---|---|---|---|---|
| 5,090,854 A | * | 2/1992 | Hafeli | F16B 39/28 411/155 |
| 7,643,867 B2 | * | 1/2010 | Solar | A61B 90/39 600/426 |
| 7,726,564 B2 | * | 6/2010 | Goldbach | A61B 90/96 235/385 |
| 2002/2015189 | | 10/2002 | Melkent et al. | |
| 2003/0225329 A1 | * | 12/2003 | Rossner | A61B 90/39 600/424 |
| 2004/0068263 A1 | * | 4/2004 | Chouinard | A61B 90/10 606/86 R |
| 2005/0113659 A1 | * | 5/2005 | Pothier | A61B 90/36 600/372 |
| 2006/0235426 A1 | | 10/2006 | Lim et al. | |

(Continued)

Primary Examiner — Jason M Ip
(74) Attorney, Agent, or Firm — Sorell, Lenna & Schmidt, LLP (57) ABSTRACT An image guide includes a member having a first surface and a second surface. The member defines a plane. The member is oriented relative to a sensor to communicate a signal representative of a position of a surgical instrument. At least one marker is connectable with the member and extends relative to the plane from the first surface and the second surface for detectable alignment with the sensor. In some embodiments, surgical systems, surgical instruments, implants and methods are disclosed.

19 Claims, 4 Drawing Sheets (56) References Cited

U.S. PATENT DOCUMENTS

| | | | |
|---|---|---|---|
| 2006/0281991 A1* | 12/2006 | Fitzpatrick | A61B 90/16 600/426 |
| 2010/0160932 A1* | 6/2010 | Gschwandtner | A61B 90/39 606/139 |
| 2010/0286713 A1 | 11/2010 | Melkent et al. | |
| 2012/0123299 A1* | 5/2012 | Neubauer | A61B 34/20 600/587 |
| 2012/0185046 A1 | 7/2012 | McKay | |
| 2014/0172105 A1 | 6/2014 | Frasier et al. | |
| 2016/0081812 A1 | 3/2016 | Waugh et al. | |
| 2016/0220389 A1 | 8/2016 | Dinville | |

* cited by examiner

SURGICAL TRACKING DEVICE AND INSTRUMENT

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, an image guide is provided. The image guide comprises a member including a first surface and a second surface. The member defines a plane. The member is oriented relative to a sensor to communicate a signal representative of a position of a surgical instrument. At least one marker is connectable with the member and extends relative to the plane from the first surface and the second surface for detectable alignment with the sensor. In some embodiments, surgical systems, surgical instruments, implants and methods are provided.

In one embodiment, the image guide includes a member defining a plane and including a transverse wall. The member is oriented relative to a sensor to communicate a signal representative of a position of a surgical instrument. At least one marker is connectable with the member and extends laterally from the wall in alignment with the plane for detectable alignment with the sensor in a plurality of orientations of the surgical instrument relative to the sensor.

In one embodiment, a surgical system is provided. The surgical system includes a surgical instrument and an image guide including a member having a first surface and a second surface, and defining a plane. The member is oriented relative to a sensor to communicate a signal representative of a position of the surgical instrument. At least one marker is connectable with the member and extends relative to the plane from the first surface and the second surface for detectable alignment with the sensor. A tracking device includes the sensor that receives the signal and communicates with a processor to generate data for display of an image from a monitor. The image represents position of the surgical instrument relative to a body.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system for preparing a surgical site, and a method for treating a spine. In some embodiments, the surgical system includes a surgical instrument having an image guide, such as, for example, a surgical navigation tracking device. In some embodiments, the surgical system includes a surgical instrument, such as, for example, an inserter employed with a selected spinal implant, such as, for example, an interbody implant, which is connected to the surgical instrument.

In some embodiments, the present surgical system includes an image guide comprising a multiple directional navigation tracker. In some embodiments, the present surgical system includes an image guide that allows repositioning of a surgical navigation tracker to change orientation of a surgical navigated instrument with respect to a sensor camera during a surgical procedure, for example, changing orientation of the surgical navigated instrument from being pointed from a first orientation to a second orientation, and/or a plurality of alternate orientations, for example, cranially to caudally and/or caudally to cranially. In some embodiments, the image guide allows markers, such as, for example, spherical fiducials to be positioned on either side or on a center plane of a tracker body. As such, the marker is visible and/or detectable from either side of the surgical instrument.

In some embodiments, the present surgical system includes an image guide comprising markers, such as, for example, pins disposed above and below a central plane of a surgical navigation tracker. In some embodiments, the image guide includes markers, such as, for example, spherical fiducials placed on either side of the tracker depending on the surgical instrument orientation and/or the sensor camera position. In some embodiments, the tracker includes markers such that the position of the markers can be changed if the desired instrument orientation is changed. In some embodiments, the image guide includes a tracker body that is machined with features that allow markers, such as, for example, pins with spherical fiducials to be re-positioned as needed enabling the spherical fiducials to be placed either above or below a central plane of the tracker body depending on sensor camera position and surgical instrument orientation. In some embodiments, the image guide includes a tracker body such that the pins lie on the central plane and allow the camera to detect and/or visually align with the spherical fiducials from either side of the surgical instrument. In some embodiments, the image guide allows orientation of the surgical instrument to be changed without having to detach and re-attach, or otherwise re-orient, the tracker.

In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide provides indicia and/or display of a precise linear position of the image guide on the surgical instrument. In some embodiments, this configuration provides indicia and/or display of an amount of manipulation, movement, translation and/or rotation of the surgical instrument and/or the implant with tissue, such as, for example, an intervertebral space.

In some embodiments, the surgical system includes a surgical instrument having one or more image guides, which include a tracker that provides location of a surgical instrument in three dimensions, and a tracker that provides location of the surgical instrument and/or a spinal implant in two dimensions, such as, for example, a selected plane. In some embodiments, this configuration provides indicia and/or display of surgical instrument and/or implant position corresponding to an amount of manipulation, movement, translation and/or rotation of the surgical instrument and/or the implant with tissue, such as, for example, an intervertebral space. In some embodiments, the surgical system includes a surgical instrument that comprises an inserter employed with a method for delivering an interbody spacer into an intervertebral disc space. In some embodiments, the method includes the step of manipulating, moving, translating and/or rotating the interbody spacer in a precise amount upon selected disposal of the interbody spacer in the intervertebral disc space.

In some embodiments, the surgical system includes a surgical instrument comprising a navigation compatible implant inserter. In some embodiments, the surgical system includes a surgical instrument having one or more image guides, which provide position and rotation indicia and/or display of an implant via a camera sensor and a computer display screen. In some embodiments, the surgical system includes a surgical inserter that has two image guide arrays. In some embodiments, the image guide arrays interact with a navigation enabled camera sensor to provide imaging during insertion and rotation of an implant.

In some embodiments, the surgical instrument includes a surgically navigated instrument, such as, for example, drills, drivers, and taps, which freely rotate about a centerline axis. In some embodiments, the surgical instrument includes a navigation tracker that is optically tracked and requires a line-of-sight view to a sensor, such as, for example, a camera. In some embodiments, the surgical system includes a navigation tracker attached to a surgical instrument and is disposed in a direct line of sight of a sensor, which includes one or more cameras. In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 1:
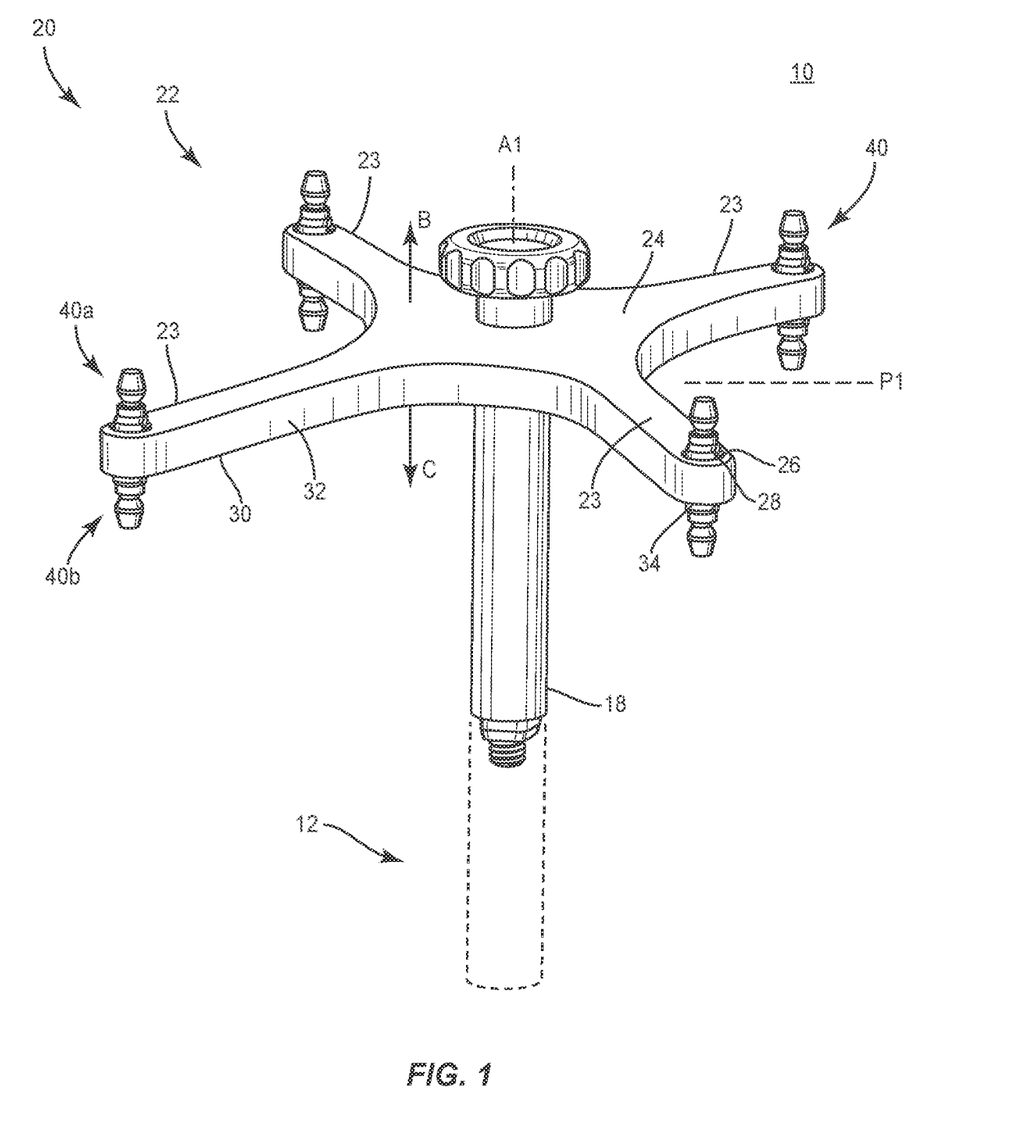
FIG. 1 is a perspective view in part phantom of components of one embodiment of a surgical system in accordance with the principles of the present disclosure.
Figure 2:
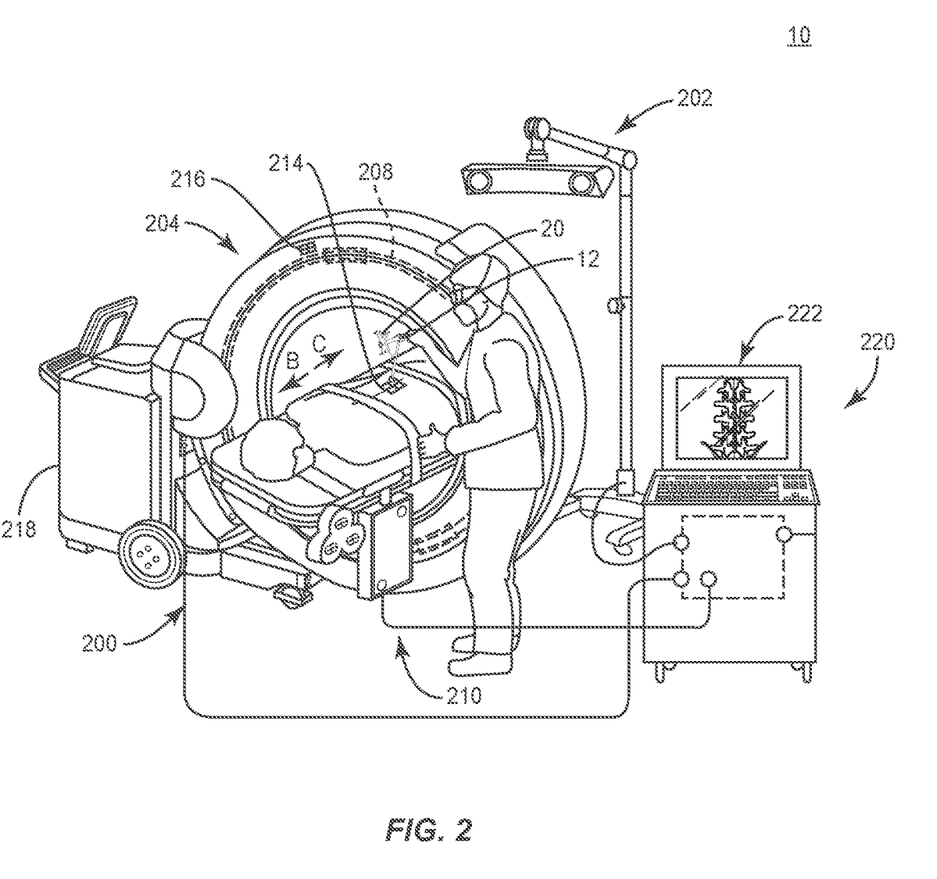
FIG. 2 is a perspective view of components of one embodiment of a surgical system in accordance with the principles of the present disclosure.

The following discussion includes a description of a surgical system including a surgical instrument, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1 and 2, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques to deliver and introduce instrumentation and/or a spinal implant to a surgical site of a patient. In some embodiments, the spinal implant can include one or more components of one or more spinal constructs, such as, for example, cages, spacers, vertebral devices, bone fasteners, spinal rods, connectors and/or plates.

Surgical system 10 comprises a surgical instrument 12. Surgical instrument 12 is configured for connection with an image guide, such as, for example, a navigation component 20, as described herein. Navigation component 20 generates a signal representative of a position of surgical instrument 12 and/or a spinal implant connected thereto, for example, relative to a portion of a patient's anatomy, a depth within the patient's anatomy and/or one or more components of surgical system 10 for display on a monitor, as described herein. In some embodiments, navigation component 20 is configured to generate a signal representative of a position of surgical instrument 12 as surgical instrument 12 is manipulated into one or more orientations relative to a sensor array 202, as described herein.

Navigation component 20 maintains communication and/or is configured to maintain detectable alignment with sensor array 202. In some embodiments, navigation component 20 maintains communication and/or detectable alignment with sensor array 202 during movement of surgical instrument 12 without having to manipulate, move, translate and/or rotate navigation component 20, relative to surgical instrument 12. As such, navigation component 20 is detectable when surgical instrument 12 is disposed in various orientations relative to sensor array 202. In some embodiments, navigation component 20 is connected with surgical instrument 12 in fixed position.

In some embodiments, an image guide as described herein, may include one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 20 is connectable with surgical instrument 12 via a post 18, which defines an axis A1. Navigation component 20 includes a tracking device having an emitter array 22. Emitter array 22 is disposed along axis A1. In some embodiments, emitter array 22 may be disposed at various orientations relative to axis A1, such as, for example, parallel, perpendicular, transverse and/or other angular orientations, such as, acute or obtuse. One or more markers 40 are disposed with emitter array 22 in detectable alignment with sensor array 202, as described herein. Emitter array 22 is configured for generating a signal to sensor array 202, as shown in FIG. 2 and described herein, representing a three-dimensional spatial position and/or a trajectory of surgical instrument 12 and/or a spinal implant connected thereto, for example, relative to a portion of a patient's anatomy, a depth within the patient's anatomy and/or one or more components of surgical system 10 for display on a monitor, as described herein.

Emitter array 22 defines a plane P1. Emitter array 22 includes four spaced apart arms 23 that extend along plane P1 and radially extend from axis A1. In some embodiments, arms 23 define a substantially X-shape. Emitter array 22 includes a surface 24. Surface 24 is oriented in a direction, as shown by arrow B in FIG. 1, relative to plane P1. In some embodiments, the direction shown by arrow B can include, such as, for example, a caudal, cranial, lateral, anterior and/or posterior direction and/or orientation. In some embodiments, surface 24 may include various surface configurations, such as, for example, smooth, grooved, rough, dimpled, polished and/or textured.

Arms 23 each include a mating surface configured for engagement with markers 40, as described herein. Markers 40 include one or more markers 40a that are engageable with a threaded surface 26 of arm 23. Each of arms 23 define a cavity 28 configured for disposal of marker 40a and include surface 26, which is threaded with a surface of marker 40a to fix marker 40a with arm 23. Cavity 28 is disposed with each of arms 23 such that marker 40a extends from surface 24, in the direction shown by arrow B in FIG. 1. Disposal of marker 40a in the direction shown by arrow B facilitates maintaining communication and/or detectable alignment of one or more markers 40a with sensor array 202 when surgical instrument 12 and/or a spinal implant connected thereto is disposed in a three-dimensional spatial position and/or a trajectory, for example, relative to a portion of a patient's anatomy, a depth within the patient's anatomy and/or one or more components of surgical system 10. In some embodiments, one or more arms 23 can include a cavity 28.

In some embodiments, one or more markers 40a are welded to emitter array 22 and/or one or more arms 23. In some embodiments, one or more markers 40a are monolithically formed with emitter array 22 and/or one or more arms 23. In some embodiments, marker 40a includes a mating surface that is forcibly snap-fit to emitter array 22 and/or one or more arms 23, for example, to a snap fit mating surface that defines at least a portion of cavity 28. In some embodiments, marker 40a includes a mating surface that is forcibly pop-fit to emitter array 22 and/or one or more arms 23, for example, to a pop-fit mating surface that defines at least a portion of cavity 28. In some embodiments, marker 40a may be connected with emitter array 22 and/or one or more arms 23 in alternate fixation configurations, such as, for example, friction fit, pressure fit, locking protrusion/recess, locking keyway and/or adhesive.

Emitter array 22 includes a surface 30. Surface 30 is oriented in a direction, as shown by arrow C in FIG. 1, relative to plane P1. Surface 30 is oriented in an alternative direction relative to the direction shown by arrow B. In some embodiments, surface 30 is oriented in a direction opposite to the direction shown by arrow B. In some embodiments, surface 30 is oriented, in a direction transverse and/or at other angular orientations, such as, acute or obtuse, to the direction shown by arrow B. In some embodiments, the direction shown by arrow C can include, such as, for example, a caudal, cranial, lateral, anterior and/or posterior direction and/or orientation. In some embodiments, surface 30 is disposed parallel to surface 24. In some embodiments, surface 30 may include various surface configurations, such as, for example, smooth, grooved, rough, dimpled, polished and/or textured. Emitter array 22 includes a wall 32 that extends laterally thereabout. Surfaces 24, 30 define at least a portion of wall 32 such that wall 32 extends therebetween.

Markers 40 include one or more markers 40b that are engageable with a threaded surface 34 of arm 23. Each of arms 23 define cavity 28, which is configured for disposal of marker 40b and includes surface 34, which is threaded with a surface of marker 40b to fix marker 40b with arm 23. Cavity 28 is disposed with each of arms 23 such that marker 40b extends from surface 30, in the direction shown by arrow C in FIG. 1. Disposal of marker 40b in the direction shown by arrow C facilitates maintaining communication and/or detectable alignment of one or more markers 40b with sensor array 202 when surgical instrument 12 and/or a spinal implant connected thereto is disposed in a three-dimensional spatial position and/or a trajectory, for example, relative to a portion of a patient's anatomy, a depth within the patient's anatomy and/or one or more components of surgical system 10. In some embodiments, one or more arms 23 can include a cavity 28.

In some embodiments, one or more markers 40b are welded to emitter array 22 and/or one or more arms 23. In some embodiments, one or more markers 40b are monolithically formed with emitter array 22 and/or one or more arms 23. In some embodiments, marker 40b includes a mating surface that is forcibly snap-fit to emitter array 22 and/or one or more arms 23, for example, to a snap fit mating surface that defines at least a portion of cavity 28. In some embodiments, marker 40b includes a mating surface that is forcibly pop-fit to emitter array 22 and/or one or more arms 23, for example, to a pop-fit mating surface that defines at least a portion of cavity 28. In some embodiments, marker 40b may be connected with emitter array 22 and/or one or more arms 23 in alternate fixation configurations, such as, for example, friction fit, pressure fit, locking protrusion/recess, locking keyway and/or adhesive.

Marker 40a includes a spherical fiducial extending from surface 24 and marker 40b includes a spherical fiducial extending from surface 30. Markers 40a, 40b extend from surfaces 24, 30 relative to plane P1 to facilitate detectable alignment and generating the signal to sensor array 202 during a surgical procedure, for example, when surgical instrument 12 and/or a spinal implant connected thereto is disposed in a three-dimensional spatial position and/or a trajectory, for example, relative to a portion of a patient's anatomy, a depth within the patient's anatomy and/or one or more components of surgical system 10. In some embodiments, surface 26 is disposed in a relative co-axial orientation with surface 34 within cavity 28 such that markers 40a, 40b are disposed in a relative co-axial orientation. In some embodiments, surfaces 26, 34 and/or markers 40a, 40b may be disposed at alternative relative orientations, such as, for example, transverse and/or other angular orientations, such as, acute or obtuse.

For example, surgical instrument 12, which includes markers 40a extending from surface 24 in the direction shown by arrow B and markers 40b extending from surface 30 in the direction shown by arrow C, is initially disposed in a first and/or selected orientation relative to sensor array 202. In one example, surgical instrument 12 and/or a spinal implant connected thereto is disposed in a three-dimensional spatial position and/or a trajectory such that surface 24 is disposed in a cranial orientation and surface 30 is disposed in a caudal orientation relative to a patient anatomy. In the first and/or selected orientation relative to sensor array 202, markers 40a are fixed with surface 24 and disposed in communication and/or detectable alignment with sensor array 202 to generate a signal to sensor array 202 representing the three-dimensional spatial position and/or trajectory of surgical instrument 12 and/or a spinal implant connected thereto, for example, relative to a portion of a patient's anatomy, a depth within the patient's anatomy and/or one or more components of surgical system 10 for display on a monitor. Markers 40b are fixed with surface 30.

During a surgical procedure, surgical instrument 12 may be manipulated, moved, translated, rotated and/or repositioned to a second and/or selected orientation relative to sensor array 202. In one example, surgical instrument 12 and/or a spinal implant connected thereto is rotated and repositioned to the second and/or selected orientation such that surface 24 and markers 40*a* are moved out of communication and/or detectable alignment with sensor array 202 and surface 30 and markers 40*b* are moved into communication and/or detectable alignment with sensor array 202. As such, surface 30 is disposed in a cranial orientation and surface 24 is disposed in a caudal orientation relative to a patient anatomy. In the second and/or selected orientation relative to sensor array 202, markers 40*b* are fixed with surface 30 and disposed in communication and/or detectable alignment with sensor array 202 to generate a signal to sensor array 202 representing the three-dimensional spatial position and/or trajectory of surgical instrument 12 and/or a spinal implant connected thereto, for example, relative to a portion of a patient's anatomy, a depth within the patient's anatomy and/or one or more components of surgical system 10 for display on a monitor. Markers 40*a* are fixed with surface 24. In some embodiments, the configuration of emitter array 22 provides multi-directional detectable alignment with sensor array 202, which allows repositioning of surgical instrument 12 and emitter array 22 relative to sensor array 202 during a surgical procedure such that markers 40 are visible and/or detectable from either side of surgical instrument 12. As such, emitter array 22 allows orientation of surgical instrument 12 to be changed without having to detach and re-attach, or otherwise re-orient, emitter array 22. In some embodiments, one or more markers 40 can be connected to emitter array 22 and/or one or more arms 23 intra-operatively.

Markers 40 appear in the image produced by a surgical navigation system 200 for use as a point of reference or a measure. Emitter array 22 generates signals representing the position of various body reference points of a patient's anatomy. In some embodiments, markers 40 include at least one light emitting diode. In some embodiments, markers 40 may include other tracking devices capable of being tracked by sensor array 202, such as, for example, a tracking device that actively generates acoustic signals, magnetic signals, electromagnetic signals, radiologic signals. In some embodiments, markers 40 may be removably attached to emitter array 22. In some embodiments, one or more of markers 40 each include a single ball-shaped marker.

Surgical instrument 12 is configured for disposal adjacent a surgical site such that navigation component 20 is oriented relative to sensor array 202 to maintain communication between navigation component 20 and sensor array 202 during a surgical procedure, as described herein. In some embodiments, sensor array 202 receives signals from navigation component 20 to provide a three-dimensional spatial position and/or a trajectory of surgical instrument 12 and/or a spinal implant connected thereto relative to a portion of a patient's anatomy and/or a depth of surgical instrument 12 within the patient's anatomy for display on a monitor. See, for example, similar surgical navigation components and their use as described in U.S. Pat. Nos. 6,021,343, 6,725, 080, 6,796,988, the entire contents of each of these references being incorporated by reference herein.

Surgical navigation system 200 is configured for acquiring and displaying medical imaging, such as, for example, x-ray images appropriate for a given surgical procedure, as shown in FIG. 2. In some embodiments, pre-acquired images of a patient are collected. In some embodiments, surgical navigation system 200 can include an O-arm® imaging device 204 sold by Medtronic Navigation, Inc. having a place of business in Louisville, Colo., USA. Imaging device 204 may have a generally annular gantry housing that encloses an image capturing portion 208.

In some embodiments, image capturing portion 208 may include an x-ray source or emission portion and an x-ray receiving or image receiving portion located generally or as practically possible 180 degrees from each other and mounted on a rotor (not shown) relative to a track of image capturing portion 208. Image capturing portion 208 can be operable to rotate 360 degrees during image acquisition. Image capturing portion 208 may rotate around a central point or axis, allowing image data of the patient to be acquired from multiple directions or in multiple planes. Surgical navigation system 200 can include those disclosed in U.S. Pat. Nos. 8,842,893, 7,188,998; 7,108,421; 7,106, 825; 7,001,045; and 6,940,941; the entire contents of each of these references being incorporated by reference herein.

In some embodiments, surgical navigation system 200 can include C-arm fluoroscopic imaging systems, which can generate three-dimensional views of a patient. The position of image capturing portion 208 can be precisely known relative to any other portion of imaging device 204. In some embodiments, a precise knowledge of the position of image capturing portion 208 can be used in conjunction with a tracking system 210 to determine the position of image capturing portion 208 and the image data relative to the patient.

Tracking system 210 can include various portions that are associated or included with surgical navigation system 200. In some embodiments, tracking system 210 can also include a plurality of types of tracking systems, such as, for example, an optical tracking system that includes an optical localizer, such as, for example, sensor array 202 and/or an EM tracking system that can include an EM localizer. Various tracking devices can be tracked with tracking system 210 and the information can be used by surgical navigation system 200 to allow for a display of a position of an item, such as, for example, a patient tracking device 214, an imaging tracking device 216, and/or an instrument tracking device, such as, for example, navigation component 20 to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to computer 218 where they may be forwarded to surgical navigation computer 220. Image transfer may be performed over a standard video connection or a digital link including wired and wireless. Computer 220 provides the ability to display, via monitor 222, as well as save, digitally manipulate, or print a hard copy of the received images. In some embodiments, images may also be displayed to the surgeon through a heads-up display.

In some embodiments, surgical navigation system 200 provides for real-time tracking of surgical instrument 12 and/or a spinal implant connected thereto. Sensor array 202 is located in such a manner to provide a clear line of sight with navigation component 20, as described herein. In some embodiments, navigation component 20 communicates with sensor array 202 via infrared technology. Sensor array 202 is coupled to computer 220, which may be programmed with software modules that analyze signals transmitted by sensor array 202 to determine the position of each object in a detector space. A processor sends the information to monitor 222, which provides a visual representation of the position of surgical instrument 12 and/or a spinal implant connected thereto relative to the patient's anatomy to allow the medical practitioner to move surgical instrument 12 to a desired location within the patient's anatomy.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body. In some embodiments, the components of surgical system 10 may be employed with one or a plurality of vertebra. To treat a selected section of vertebrae, a medical practitioner obtains access to a surgical site in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including surgical instrument 12 having navigation component 20, as described herein, adjacent an area within the patient's body. Surgical instrument 12 may be utilized to prepare tissue surfaces of vertebrae and/or facilitate insertion of a spinal implant. Surgical instrument 12, as shown in FIG. 2, includes a distal and/or working end connected with a drill bit for creating one or more pilot holes in tissue for disposal of implants. In some embodiments, surgical instrument 12 includes a distal and/or working end that includes an implant inserter for disposing a spinal implant with tissue.

Surgical instrument 12 includes markers 40a extending from surface 24 and markers 40b extending from surface 30, as described herein. A practitioner manipulates surgical instrument 12 for creating a pilot hole in vertebral tissue such that surface 24 is disposed in a cranial orientation, in the direction shown by arrow B in FIG. 2, and surface 30 is disposed in a caudal orientation, in the direction shown by arrow C in FIG. 2, relative to the patient. Markers 40a are fixed with surface 24 and disposed in communication and/or detectable alignment with sensor array 202 to generate a signal to sensor array 202 representing the three-dimensional spatial position of surgical instrument 12 for display on monitor 222, as described herein. Markers 40b are fixed with surface 30. Surgical navigation system 200 provides for real-time tracking of surgical instrument 12 and a visual representation of the position of surgical instrument 12 relative to the patient's anatomy.

During the surgical procedure, repositioning of surgical instrument 12 may be performed to facilitate removal of tissue and/or spinal implant placement. Surgical instrument 12 is rotated and repositioned to a selected orientation such that surface 24 and markers 40a are moved out of communication and/or detectable alignment with sensor array 202, and surface 30 and markers 40b are moved into communication and/or detectable alignment with sensor array 202. As such, surface 30 is disposed in a cranial orientation and surface 24 is disposed in a caudal orientation relative to a patient anatomy. Markers 40b are fixed with surface 30 such that communication and/or detectable alignment of emitter array 22 with sensor array 202 is maintained. Markers 40b generate a signal to sensor array 202 representing the three-dimensional spatial position of surgical instrument 12, as described herein, for display on monitor 222. Emitter array 22 provides multi-directional detectable alignment with sensor array 202. Surgical instrument 12 is repositionable relative to sensor array 202 during a surgical procedure such that markers 40 are visible and/or detectable from either side of surgical instrument 12. Emitter array 22 allows orientation of surgical instrument 12 to be changed without having to detach and re-attach, or otherwise re-orient, emitter array 22.

In some embodiments, surgical instrument 12 includes a distal and/or working end that may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with the vertebrae. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical system 10 are removed from the surgical site and the incision is closed.

Figure 3:
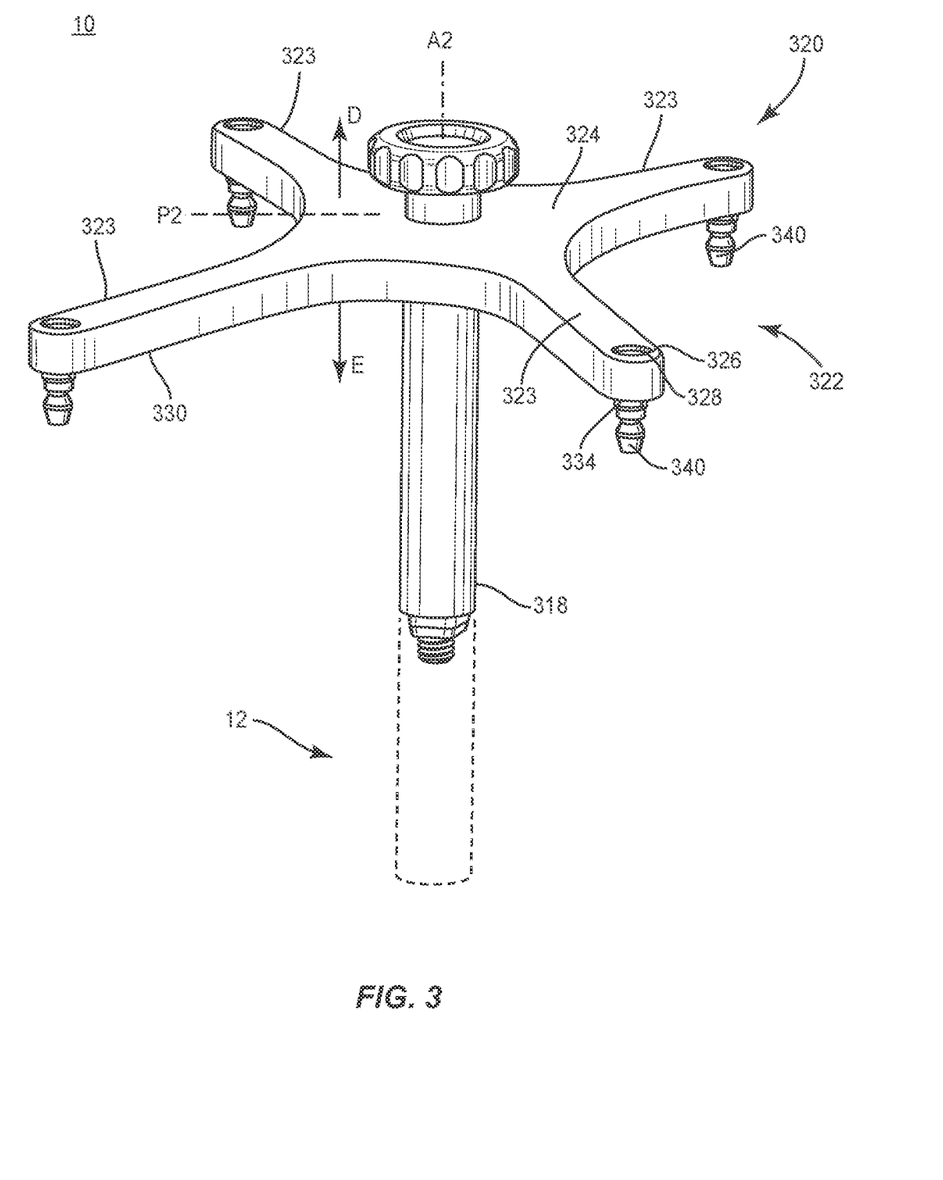
FIG. 3 is a perspective view in part phantom of components of one embodiment of a surgical system in accordance with the principles of the present disclosure.

In one embodiment, as shown in FIG. 3, surgical system 10, similar to the systems and methods described above with regard to FIGS. 1 and 2, includes surgical instrument 12, as described herein, configured for connection with an image guide, such as, for example, a navigation component 320, similar to navigation component 20 described herein. Navigation component 320 is connectable with surgical instrument 12 via a post 318, which defines an axis A2. Navigation component 320 includes a tracking device having an emitter array 322, similar to emitter array 22, disposed along axis A2. One or more markers 340, similar to markers 40 described herein, are disposed with emitter array 322 in detectable alignment with sensor array 202, as described herein.

Emitter array 322 defines a plane P2. Emitter array 322 includes four spaced apart arms 323, similar to arms 23 described herein, which extend along plane P2 and radially extend from axis A2. Emitter array 222 includes a surface 324, similar to surface 24 described herein. Arms 323 each include a mating surface configured for engagement with markers 340. Markers 340 are engageable with a threaded surface 326 of arm 323 adjacent surface 324.

Each of arms 323 define a cavity 328 configured for disposal of marker 340 and include surface 326, which is threaded with a surface of marker 340 to fix marker 340 with arm 323 adjacent surface 324. Cavity 328 is disposed with each of arms 323 and marker 340 is threaded with surface 326 such that marker 340 can be attached with emitter array 322 to extend from surface 324, in the direction shown by arrow D in FIG. 3. Disposal of marker 340 in the direction shown by arrow D facilitates maintaining communication and/or detectable alignment of one or more markers 340 with sensor array 202 when surgical instrument 12 and/or a spinal implant connected thereto is disposed in a three-dimensional spatial position and/or a trajectory, for example, relative to a portion of a patient's anatomy, a depth within the patient's anatomy and/or one or more components of surgical system 10.

Emitter array 322 includes a surface 330, similar to surface 30 described herein. Markers 340 are engageable with a threaded surface 334 of arm 323 adjacent surface 330. Cavity 328 is configured for disposal of marker 340 and includes surface 334, which is threaded with a surface of marker 340 to fix marker 340 with arm 323 adjacent surface 330. Cavity 328 is disposed with each of arms 323 such that marker 340 can be attached with emitter array 322 to extend from surface 330, in the direction shown by arrow E in FIG. 3. Disposal of marker 340 in the direction shown by arrow E facilitates maintaining communication and/or detectable alignment of one or more markers 340 with sensor array 202 when surgical instrument 12 and/or a spinal implant connected thereto is disposed in a three-dimensional spatial position and/or a trajectory, for example, relative to a portion of a patient's anatomy, a depth within the patient's anatomy and/or one or more components of surgical system 10.

Markers 340 are disposable with cavity 328 and removably attachable with surfaces 326, 334 such that markers 340 are extendable from emitter array 322 in one or a plurality of orientations, for example, in the direction shown by arrows D, E. In some embodiments, markers 340 are connectable with emitter array 322 in a plurality of detectable alignments to facilitate generating a signal to a sensor array 202. In some embodiments, markers 340 are intra-operatively attachable, removable and re-attachable with emitter array 322 such that during a surgical procedure markers 340 are moveable to facilitate maintaining communication and alignment and to at least one alternative position for detection by sensor array 202. In some embodiments, markers 340 are intra-operatively adjustable with emitter array 322 such that during a surgical procedure, markers 340 are moveable to facilitate maintaining communication and alignment and or realignment to at least one alternative position for detection by sensor array 202.

For example, surgical instrument 12 includes markers 340 threaded with surface 326 such that markers 340 are attached with emitter array 322 to extend from surface 324, as described herein. A practitioner manipulates surgical instrument 12 to prepare tissue surfaces of vertebrae and/or facilitate insertion of a spinal implant such that surface 324 is disposed in a cranial orientation and surface 330 is disposed in a caudal orientation relative to the patient. Markers 340 are fixed with surface 324 and disposed in communication and/or detectable alignment with sensor array 202 to generate a signal to sensor array 202 representing the three-dimensional spatial position of surgical instrument 12 for display on monitor 222, as described herein. During the surgical procedure, repositioning of surgical instrument 12 may be performed to facilitate removal of tissue and/or spinal implant placement. Surgical instrument 12 is rotated and repositioned to a selected orientation such that surface 324 and markers 340 are moved out of communication and/or detectable alignment with sensor array 202. Markers 340 are removed from surfaces 326 and re-attached with surface 330 such that markers 340 are threaded with surfaces 334 and maintain communication and/or detectable alignment with sensor array 202 to generate a signal to sensor array 202 representing the three-dimensional spatial position of surgical instrument 12, as described herein.

In some embodiments, marker 340 includes a mating surface that is forcibly snap-fit to emitter array 322 and/or one or more arms 323, for example, to a snap fit mating surface that defines at least a portion of cavity 328. In some embodiments, marker 340 includes a mating surface that is forcibly pop-fit to emitter array 322 and/or one or more arms 323, for example, to a pop-fit mating surface that defines at least a portion of cavity 328.

Figure 4:
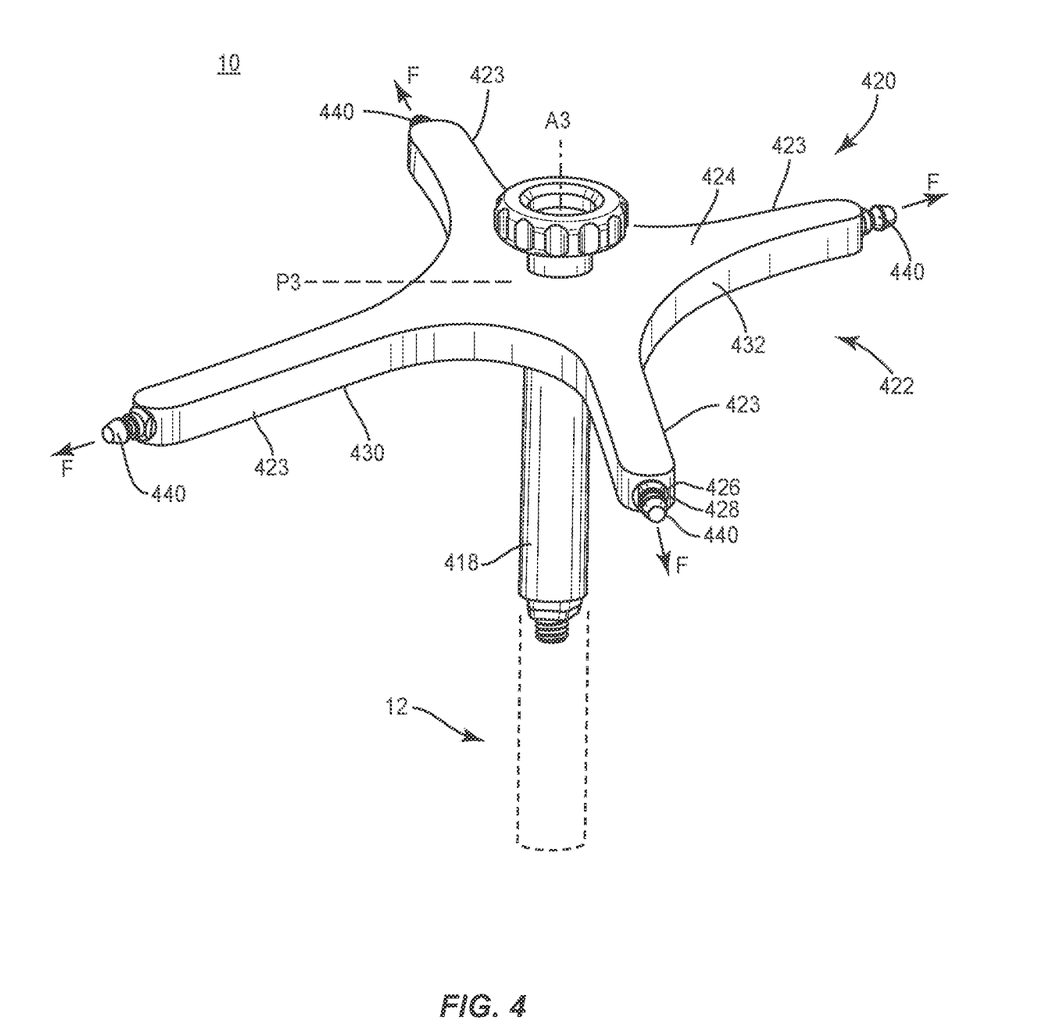
FIG. 4 is a perspective view in part phantom of components of one embodiment of a surgical system in accordance with the principles of the present disclosure.

In one embodiment, as shown in FIG. 4, surgical system 10, similar to the systems and methods described herein, includes surgical instrument 12, as described herein, configured for connection with an image guide, such as, for example, a navigation component 420, similar to navigation component 20 described herein. Navigation component 420 is connectable with surgical instrument 12 via a post 418, which defines an axis A3. Navigation component 420 includes a tracking device having an emitter array 422, similar to emitter array 22, disposed along axis A3. One or more markers 440, similar to markers 40 described herein, are disposed with emitter array 422 in detectable alignment with sensor array 202, as described herein.

Emitter array 422 defines a plane P3. Emitter array 422 includes four spaced apart arms 423, similar to arms 23 described herein, which extend along plane P3 and radially extend from axis A3. Emitter array 422 includes surfaces 424, 430, similar to surfaces 24, 30 described herein. Emitter array 422 includes a wall 432 that extends laterally thereabout. Surfaces 424, 430 define at least a portion of wall 432 such that wall 432 extends therebetween. Arms 423 each include a mating surface configured for engagement with markers 440. Markers 440 are engageable with a threaded surface 426 of arm 423 adjacent wall 432.

Each of arms 423 define a cavity 428 configured for disposal of marker 440 and include surface 426, which is threaded with a surface of marker 440 to fix marker 440 with arm 423. Cavity 428 is disposed with each of arms 423 such that marker 440 extends laterally from wall 432 and transverse relative to axis A3, in the direction shown by arrow F in FIG. 4. Disposal of marker 440 in the direction shown by arrow F facilitates maintaining communication and/or detectable alignment of one or more markers 440 with sensor array 202 when surgical instrument 12 and/or a spinal implant connected thereto is disposed in a three-dimensional spatial position and/or a trajectory, for example, relative to a portion of a patient's anatomy, a depth within the patient's anatomy and/or one or more components of surgical system 10. In some embodiments, one or more arms 423 can include a cavity 428. In some embodiments, marker 440 may extend from wall 432 in various orientations relative to axis A3 and/or plane P3, such as, for example, parallel, perpendicular, transverse and/or other angular orientations, such as, acute or obtuse, offset and/or staggered.

Markers 440 are connected with each of arms 423 in alignment with plane P3 and centrally disposed with wall 432. Markers 440 extend laterally from wall 432 to maintain communication and detectable alignment of markers 440 with sensor array 202 as surgical instrument 12 is manipulated, moved, positioned and/or re-oriented into various orientations, as described herein, relative to sensory array 202 during a surgical procedure, as described herein.

In some embodiments, one or more markers 440 are welded to emitter array 422 and/or one or more arms 423. In some embodiments, one or more markers 440 are monolithically formed with emitter array 422 and/or one or more arms 423. In some embodiments, marker 440 includes a mating surface that is forcibly snap-fit to emitter array 422 and/or one or more arms 423, for example, to a snap fit mating surface that defines at least a portion of cavity 428. In some embodiments, marker 440 includes a mating surface that is forcibly pop-fit to emitter array 422 and/or one or more arms 423, for example, to a pop-fit mating surface that defines at least a portion of cavity 428. In some embodiments, marker 440 may be connected with emitter array 422 and/or one or more arms 423 in alternative fixation configurations, such as, for example, friction fit, pressure fit, locking protrusion/recess, locking keyway and/or adhesive.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An image guide comprising:
   a member including a first surface and a second surface, the member being oriented relative to a sensor to communicate a signal representative of a position of a surgical instrument, the first surface defining a first cavity, the second surface defining a second cavity, the second cavity being coaxial with the first cavity;
   a post including opposite first and second ends, the first end extending through the first and second surfaces to connect the post with the member such that the member is permanently fixed relative to the post to prevent relative movement between the post and the member, the second end being configured for connection with the surgical instrument;
   a knob coupled to the first end such that the first and second surfaces are positioned between the knob and the second end; and
   at least one marker for detectable alignment with the sensor, the at least one marker being movable between a first configuration in which the at least one marker is positioned in the first cavity and extends outwardly from the first surface and a second configuration in which the at least one marker is positioned in the second cavity and extends outwardly from the second surface.

2. The image guide recited in claim 1, wherein the first surface defines a first thread and the second surface defines a second thread, the at least one marker comprising a third thread configured for engagement with the first thread and the second thread.

3. The image guide recited in claim 1, wherein the at least one marker is intra-operatively connectable with the member.

4. The image guide recited in claim 1, wherein the member comprises a body and four spaced apart arms extending from the body, one of the arms including the first cavity and the second cavity.

5. The image guide recited in claim 4, wherein the body has a maximum diameter that is greater than a maximum diameter of the knob.

6. The image guide recited in claim 1, wherein the at least one marker includes a light emitting diode.

7. The image guide recited in claim 1, wherein the at least one marker is connectable with the member in a friction-fit engagement.

8. The image guide recited in claim 1, wherein the at least one marker is connectable with the member in a snap-fit engagement.

9. The image guide recited in claim 1, wherein the at least one marker includes a plurality of spherical fiducials spaced apart and disposed about the member.

10. The image guide recited in claim 1, wherein the at least one marker includes a first spherical fiducial extending from the first surface and a second spherical fiducial extending from the second surface, the fiducials being disposed in a co-axial alignment.

11. The image guide recited in claim 1, wherein the first surface is connected to the second surface by a transverse wall.

12. The image guide recited in claim 1, wherein the post is fixed relative to the member.

13. The image guide recited in claim 1, wherein the member includes spaced apart arms extending in the plane, each of the arms including a marker extending from the first and second surfaces.

14. An image guide comprising:
    a member defining a plane and including a transverse wall, the member being oriented relative to a sensor to communicate a signal representative of a position of a surgical instrument, the transverse wall defining a cavity;
    a post including opposite first and second ends, the first end extending through a thickness of the member defined by transverse wall to connect the post with the member, the member being permanently fixed relative to the post to prevent relative movement between the post and the member, the second end being configured for connection with the surgical instrument;
    a knob coupled to the first end such that the member is positioned between the knob and the second end, the knob comprising a plurality of spaced apart indents disposed circumferentially about an outer surface of the knob; and
    at least one marker extending along a longitudinal axis between opposite top and bottom ends, the bottom end being disposed in the cavity such that the longitudinal axis extends perpendicular to the post and the at least one marker extends laterally from the transverse wall in alignment with the plane for detectable alignment with the sensor in a plurality of orientations of the surgical instrument relative to the sensor.

15. The image guide recited in claim 14, wherein the member includes spaced apart arms extending in the plane, each of the arms including a marker.

16. A surgical system comprising:
    a surgical instrument;
    an image guide including a member having a first surface and a second surface and defining a plane, the member being oriented relative to a sensor to communicate a signal representative of a position of the surgical instrument, the first surface defining a first cavity, the second surface defining a second cavity, the second cavity being coaxial with the first cavity;
a post including opposite first and second ends, the first end extending through the first and second surfaces to connect the post with the member such that the member is permanently fixed relative to the post to prevent relative movement between the post and the member, the second end comprising a threaded outer surface that engages a threaded inner surface of the surgical instrument to connect the post to the surgical instrument;
a knob coupled to the first end such that the first and second surfaces are positioned between the knob and the second end;
at least one marker being connectable with the member for detectable alignment with the sensor, the at least one marker being movable between a first configuration in which the at least one marker is positioned in the first cavity and extends outwardly from the first surface and a second configuration in which the at least one marker is positioned in the second cavity and extends outwardly from the second surface; and
a tracking device including the sensor that receives the signal and communicates with a processor to generate data for display of an image from a monitor, the image representing position of the surgical instrument relative to a body.

17. The surgical system recited in claim 16, wherein the first surface defines a first thread and the second surface defines a second thread, the at least one marker comprising a third thread configured for engagement with the first thread and the second thread.

18. The surgical system recited in claim 16, wherein the post is fixed relative to the member.

19. The surgical system recited in claim 16, wherein the knob has a maximum diameter that is greater than a maximum diameter of the post.

* * * * *